United States Patent [19]

Edwards

[11] Patent Number: 5,441,634

[45] Date of Patent: Aug. 15, 1995

[54] APPARATUS AND METHOD OF CIRCULATING A BODY OF FLUID CONTAINING A MIXTURE OF SOLID WASTE AND WATER AND SEPARATING THEM

[75] Inventor: Haskell Edwards, Exeter, Calif.

[73] Assignee: Edwards Laboratories, Inc., Exeter, Calif.

[21] Appl. No.: 88,192

[22] Filed: Jul. 6, 1993

[51] Int. Cl.⁶ .............................................. C02F 3/00
[52] U.S. Cl. .................... 210/194; 210/195.3; 210/220; 210/262; 210/629
[58] Field of Search ...................... 210/188, 194, 195.1, 210/195.3, 195.4, 197, 219, 220, 221.2, 258, 259, 261, 262, 603, 605, 620, 621, 629, 630, 903, 532.2

[56] References Cited

U.S. PATENT DOCUMENTS

| | | | |
|---|---|---|---|
| 924,664 | 6/1909 | Imhoff | 210/532.2 |
| 978,889 | 12/1910 | Imhoff | 210/195.4 |
| 2,613,180 | 10/1952 | Green et al. | 210/195.4 |
| 3,043,433 | 7/1962 | Singer | 210/629 |
| 3,092,678 | 6/1963 | Braun | 210/629 |
| 3,339,741 | 9/1967 | Bernard et al. | 210/195.4 |
| 3,701,727 | 10/1972 | Kormanik | 210/605 |
| 3,817,857 | 6/1974 | Torpey | 210/605 |
| 3,929,640 | 12/1975 | Dohnert | 210/195.4 |
| 4,211,657 | 7/1980 | Etlin | 210/195.4 |
| 4,530,762 | 7/1985 | Love | 210/194 |
| 4,568,457 | 2/1986 | Sullivan | 210/151 |
| 4,604,206 | 8/1986 | Sullivan | 210/603 |
| 4,609,460 | 9/1986 | Vellinga | 210/603 |
| 4,622,147 | 11/1986 | Vellinga | 210/539 |
| 4,758,339 | 7/1988 | Vellinga | 210/539 |
| 4,772,396 | 9/1988 | Voyt | 210/605 |

OTHER PUBLICATIONS biothane ® "Anaerobic Wastewater Treatment Process", AER-O-FLO Manufacturing Sewage Treatment Systems, 3 pages, double-sided, printed in USA, May 1984.

PE ® Technical Publishing "Plant Engineering Directory and Specifications Catalog ®", cover page and pages K-14 to -K16 and K18-K23, 1985.

BIOPAQ by Paques Lavalin, "Anaerobic Wastewater Treatment", 3 pages, double-sided.

Biothane ® Digest, vol. 2, No. 1, 2 pages, double-sided, Winter, 1982.

"Water Treatment Methods", Practical Fossil Plant Technology, Third Edition, General Physics Corporation, pp. 11-17 to 11-26, Columbia, Md., 1981.

*Primary Examiner*—Christopher Upton
*Attorney, Agent, or Firm*—Darby & Darby

[57] ABSTRACT

An apparatus and method of creating circulation of a mixture containing solid waste and water such as sludge and separating these components. The apparatus includes a tank housing, in inverted funnel-like element within the housing for constricting upward flow of a gasborne mixture, a trapped gas pocket for degassing the gasborne mixture, a containment element interposed between an effluent weir and the inverted funnel for directing downward and outward flow of the degassed mixture, and a deflecting surface in the path of the downward flow to promote settling of the solids from the degassed mixture and for allowing clarified water to rise within the containment element and the tank housing to reach the effluent weir. For aerobic treatment, a diffuser is arranged within the inverted funnel to supply air or gas to create upward flow of the gasborne mixture. For anaerobic treatment, the tank housing is atop a digester containing a sludge blanket and anaerobic bacteria produce biogas to propel an upward flow of the gasborne mixture.

15 Claims, 7 Drawing Sheets

APPARATUS AND METHOD OF CIRCULATING A BODY OF FLUID CONTAINING A MIXTURE OF SOLID WASTE AND WATER AND SEPARATING THEM

BACKGROUND OF THE INVENTION

1. Field of the Invention

The present invention relates to an apparatus and method of handling a circulating body of fluid containing solid waste and water, such as wastewater sludge, to effect their separation. (Although the present invention is described in connection with wastewater sludge, it is to be understood that the invention is applicable to wastewater in general whether containing sludge or otherwise.) Such an apparatus and method has application for achieving suspended solid removal, acidity treatment, upflow anaerobic sludge blanket digestion, polishing treatment, activated sludge treatment, grit separation and removal, hydrolysis of primary and secondary sludge, anaerobic and aerobic treatment of primary and secondary sludge, and suspended solid precipitation. They can also be employed in high performance compact reactors.

2. Discussion of Background

There are many industrial, municipal sanitation and other processes that require the confinement and agitation of large standing bodies of liquid with concurrent heating or cooling to control their temperature. The presence of a solid phase within the liquid generally necessitates a) continuing agitation of it in order to suspend the solid more uniformly and, simultaneously, b) maintaining a substantially uniform optimum temperature throughout the liquid. Sewage digestion systems often require such agitation and temperature control, especially in anaerobic sewage systems where really vigorous agitation in the open atmosphere is not possible. At the same time, direct contact of moving mechanical parts with the body of liquid or the solids dispersed therein are to be avoided, because of the nature of the solids often encountered in such systems. Reliability, ease of servicing and maintenance, and the avoidance of any interference with the biological or chemical processes taking place in the liquid are further important criteria that must be met. For a general understanding of the engineering behind such processes and suitable implementing equipment, see Plant Engineering Directory and Specifications Catalog, © Technical Publishing 1985, Division K on Environmental Control and Water Pollution Control, pages K-14 to K-23, whose contents are incorporated herein by reference.

Sewage digestion systems treat wastewater sludge in a tank while continuously circulating the tank's contents and discharging treated effluent. Generally, a clarifier is provided with a level area to allow water to flow evenly over the surface of a weir as well as for settlement of larger organisms such as protozoa. The clarifier also has an inlet arranged to prevent the entrance velocity of the treated effluent from causing clarifier "short-circuiting" because a water current is created in the clarifier.

Wastewater biomass sludge may be in the form of either primary sludge (i.e., sludge not yet acted upon by active waste organisms) or secondary active sludge (i.e., sludge already acted upon by active waste organisms). Such active waste organisms are commonly found in such biomass sludges, but are generally too small to settle in a clarifier before the effluent is discharged. On the other hand, bacteria-consuming protozoa are developed naturally in biomass, and have greater density and will settle in the clarifier. Protozoa is commonly found in soil, cattle and other ruminant animals and where organic residues and bacteria appear.

Typical active waste organisms include aerobic bacteria and anaerobic bacteria Aerobic bacteria require dissolved oxygen for sustenance and are incapable of independent movement. Therefore, thorough mixing of water, dissolved oxygen, aerobic bacteria, together with larger bacteria-consuming organisms, is required for effective aerobic treatment.

Anaerobic bacteria, on the other hand, thrive on oxygen from their food supply and anaerobic treatment systems often employ an upflow anaerobic sludge blanket digester (hereinafter "UASB"). Typically, wastewater entering from the bottom of the UASB passes through a granular anaerobic sludge layer (i.e., the blanket), where the anaerobic bacteria digest some of the organic matter present in the wastewater and biogas (a mixture of methane and carbon dioxide) is generated. The biogas bubbles become the propellant for the upward flow of sludge particles attached to the bubbles. A gas collector dome is arranged centrally at the top of the UASB to collect the rising gas and the sludge particles are there degassed. The degassed sludge then travels downwardly because of gravity and is deflected by upper surfaces of inclined baffles in the UASB, causing the solids to settle preliminarily on the surfaces and accumulate, and then to drop off either to recirculate with the upward flow of fresh biogas or else settle to the bottom of the digester. Thus, the upward flow of the gasborne sludge in combination with the return downward flow of degassed sludge creates continuous convection and promotes sludge-wastewater contact without the need for energy-consuming mechanical or hydraulic agitation within the digester.

Conventional UASB construction and operation, however, has been found lacking in at least two respects. On the one hand, it has become clear that municipal wastewater, with its relatively high levels of suspended solids, is not an ideal fluid to be handled by, or treated in, an UASB, because such suspended solids tend to coat surfaces and plug conduits and openings, and, thereby, encourage bacteria to develop within the UASB. By contrast, high strength industrial wastewater often contains relatively high levels of chemical oxygen demand (COD) or biochemical oxygen demand (BOD) and dissolved solids, but relatively low levels of suspended solids, and, therefore, tends to be a more suitable medium for UASB handling.

On the other hand, it is also clear that, to the extent current UASB design necessitates removal of treated or separated effluent from essentially the same zone wherein gasborne sludge is being degassed, deleterious materials that contaminate the effluent can also be removed, because a typical UASB baffle system alone cannot assure effluent freedom from such contaminants.

SUMMARY OF THE INVENTION

The present invention is directed to an apparatus and method of creating circulation of a body of fluid containing solid waste and water, such as wastewater sludge, for the purpose of separating its components. The apparatus includes a mixing, aerating and separating device (hereinafter "MASD") that circulates flow within the body of fluid by constricting upward flow of a gasborne mixture and subsequently degassing the mixture to promote its downward flow due to gravity, deflects the downward flow of the degassed mixture so that solids settle out of the degassed mixture, and allows the remaining fluid that is substantially free of the settled solids to rise and reach an effluent weir. While rising, this remaining fluid is contained or isolated from the rest of the body of fluid so as to avoid contamination before its removal.

The MASD includes a vertical containment cylinder and, preferably, a constriction element having a smaller cross-section. This constriction element may be an inverted funnel having a lower portion in the form of an inverted truncated cone or bell and an upper portion in the form of a hollow neck. The MASD is within a tank that has an effluent weir, a clarifier, and deflecting surfaces that incline downwardly and inwardly.

The constriction element promotes mixing by constricting the upward flow of the gasborne mixture. After emerging from the constriction element, the gasborne mixture reaches an area where it degasses, which causes the degassed mixture to flow downwardly. Some of the degassed mixture follows the outer contour of the constriction element, thereby flowing outwardly as well as downwardly. The deflecting surface of the tank is in the path of this downward and outward flow and is spaced from the bottom of the constriction element. As a result, solids settle on the deflecting surface, eventually accumulating to slide off the inclined deflecting surface and either become caught in fresh upward flow through the constriction element or settle towards the bottom. The remaining fluid in the mixture, now substantially free of the settled solids, rises to reach the clarifier and then be discharged through the effluent weir. While rising, this remaining fluid is separated from the rest of the contents of the tank by the cylinder so as to avoid contamination from degassed mixture whose solids have not yet settled out.

For aerobic treatment, a gas diffuser or comparable mechanical device is positioned within the constriction element, preferably at its base, to supply sufficient oxygen to sustain aerobic bacteria and to bubble upwardly to create the upward flow.

For anaerobic treatment, on the other hand, a digester, containing an anaerobic bacteria sludge blanket, is arranged at a lower elevation than the MASD. The anaerobic bacteria feeds on nutrients in the influent and gives off biogas that bubbles upwardly to propel the upward flow. The top of the tank is sealed by a dome, which contains a gaseous medium above the fluid in the tank. When the biogas reaches the gaseous medium, gasborne mixture particles become detached from the gas and fall downwardly because of gravity. Deflecting surfaces are arranged to move the rising gasborne sludge into the constriction element and to prevent its entry into a zone where the remaining fluid of the degassed mixture is rising to reach the clarifier and effluent weir.

BRIEF DESCRIPTION OF THE DRAWINGS

For a better understanding of the present invention, reference is made to the following description and accompanying drawings, while the scope of the invention is set forth in the appended claims.

DESCRIPTION OF THE PREFERRED EMBODIMENTS

In each of the embodiments of FIGS. 1–7, the general principal of operation calls for creating a continuous circulation in a tank holding a body of fluid. Each embodiment has a MASD, which is responsible for constricting upward flow, degassing, compelling downward and outward flow, and deflecting the downward flow to cause solids to settle out of the fluid and clarified water to rise and remain uncontaminated until discharged through an effluent weir. Preferably, the amount of effluent being removed should substantially equal the amount of influent entering.

Figure 1:
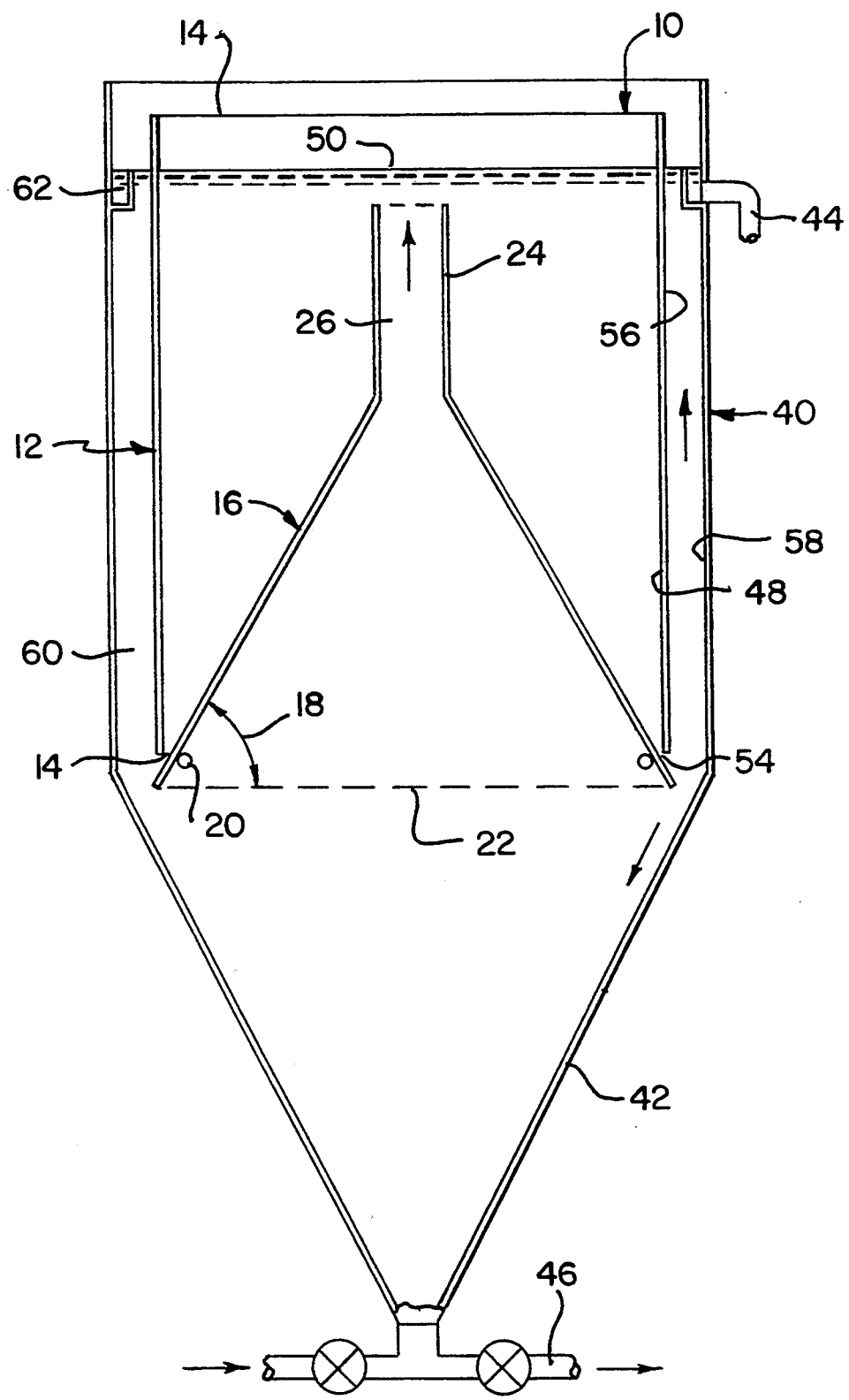
FIG. 1 is a vertical cross section of the basic elements of an MASD in a cylindrical tank in accordance with the invention. The MASD and tank are symmetrical about their respective vertical axes.

FIG. 1 shows an MASD 10 in which mixing, aeration and solid separating and settling take place in accordance with the present invention. The MASD includes a vertical containment cylinder 12 open at both ends 14, an inverted funnel element 16 having an inverted truncated cone or bell 22 with, preferably, an angle of inclination 18 of about seventy (70°) degrees, a hollow neck portion 24, and, preferably, an annular aeration tube 20 located near the base of bell 22 and within the interior space bounded thereby. Tube 20 has micropores to allow compressed air or the like to create a lifting and mixing force within bell 22. Hollow neck 24 forms and bounds a restricted space 26.

Material for tube 20 is available from a variety of different manufacturers. It is made by processing powdered synthetic rubber through an extruding device. The tubing produced contains micropores throughout the tube. Gilmore Manufacturing Company P.O. Box 838 Somerset, Pa. 15501-0838 is one of the suppliers of this type of material. The tubing is sold for use as a surface or sub-surface irrigation system.

Containment cylinder 12 and funnel 16 are supported by a separator tank 40 in any conventional manner such as by a plurality of legs of suitable strength extending in generally transverse directions, inclining from the bottom of the funnel along and around the bottom of the cylinder, to the inside of tank 40.

As shown in FIG. 1., MASD 10 can be placed inside a vertical tank 40 that has a second cone portion 42 at its bottom and, near the top of tank 40, is a clarified water effluent weir 44. Below tank cone 42 is a drain 46 to allow settled material to be removed.

In the operation of the MASD of FIG. 1, water containing suspended solids is directed into the top of tank 40 or into the bottom of the tank cone 42, depending on the intended use of the unit. If the influent is directed into the top of the tank 40, it will be discharged from within the confines of the interior surfaces 48 of cylinder 12 at or near the center. The top of cylinder is elevated above the water line 50 of the tank and, as a consequence, water and suspended solids must flow down, i.e., between cylinder and funnel 16. By supplying compressed air or other suitable gases to tube 20, the air or gas rises to the surface, drawing water and suspended solids with it into funnel 16.

Tank cone 42 in any of the embodiments preferably has a sixty (60°) degree angle of inclination and the tank is composed of stainless steel. Preferably, a similarly angled inverted truncated cone is used in the MASD. Steel reinforced concrete, fiberglass and cross linked plastic are suitable alternatives to stainless steel for the tank material. Large diameter tanks may need steel reinforced concrete construction for appropriate strength. Square and rectangle tanks may be fitted with rectangularly pyramid-shaped MASDs.

As water and suspended solids pass into funnel bell 22, pressure and turbulence increase because bell 22 constricts the upward flow. When the water and suspended solids reach the top of hollow neck 24, the solids remain within cylinder 12. The top of cylinder 12 is above the water line 50, so that material that has been forced up through the funnel 16 must then flow downwardly between interior surface 48 of cylinder 12 and exterior surface 52 of the outwardly flaring bell 22.

When the solids descend down exterior surface 52 because of gravity, they enter annular space 54 at and about the bottom edge of bell 22. There, the lifting force created by the compressed air or gas being pumped out of tube 20 located just inside the base of bell 22 creates a current that draws water and some of the settling solids back into funnel 16. This force also exerts a pulling effect on most of the settling solids, which, coupled with gravity, causes a more complete separation of the solids from the water flowing up containment zone 60 (an annular column between exterior surface 56 of cylinder 12 and interior surface 58 of tank 40) until it reaches, near the top of tank 40, a clarifier 62 from which it leaves over effluent weir 44. The degree of clarification of the effluent is dependent on: the particle size of the suspended solids; the speed at which the water rises in containment zone 60, and the degree of "short circuiting" at weir 44. Such "short circuiting" is minimized or prevented by putting the clarifier 62 at or near the top of tank 40, rather than further down its vertical height.

MASD USED IN AN ACTIVATED SLUDGE PROCESS

The activated sludge process involves water containing biodegradable waste nutrients, aerobic bacteria that absorb soluble nutrients from water, a continuous supply of dissolved oxygen and a method of mixing that will insure continuous contact of nutrients and bacteria. Bacteria are too small to settle in a clarifier; therefore larger organisms (protozoa) are also required in the activated sludge process. Protozoa will consume the bacteria which have absorbed the soluble nutrients from the water and these larger bacteria consuming organisms are capable of settling in a clarifier.

The activated sludge process requires a tank to react water-soluble nutrients with bacteria and larger bacteria-consuming organisms (protozoa, etc.), a clarifier to allow the activated sludge to settle, provision for returning activated sludge to the aeration tank and provision for removing excess activated sludge. Such components are shown in or suggested by FIGS. 1 and 2.

MASD IN A HIGH PERFORMANCE COMPACT REACTOR

Figure 2:
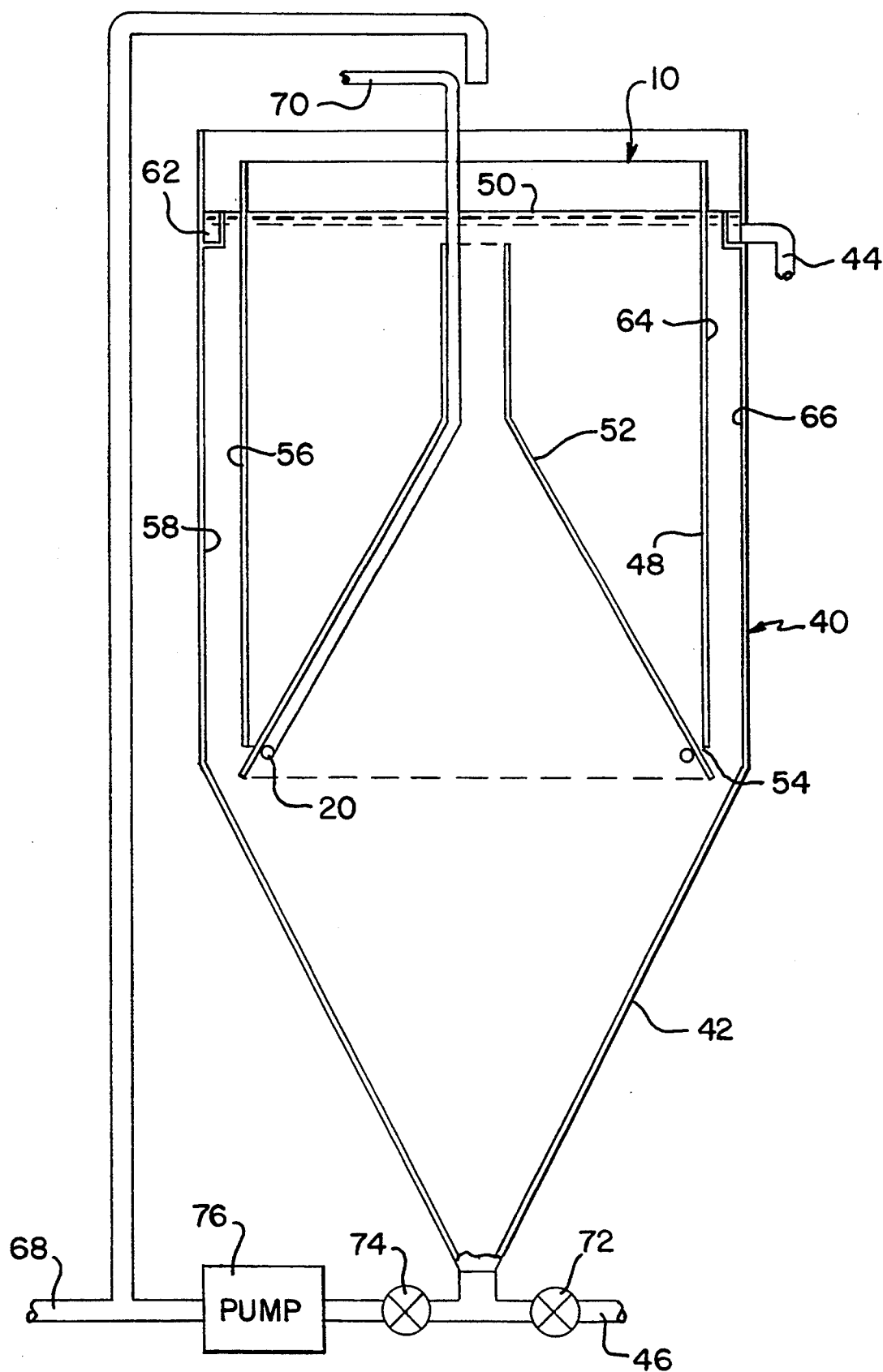
FIG. 2 is a vertical cross section of the MASD of FIG. 1 configured to operate as a high performance compact reactor.

FIG. 2 shows a vertical tank 40 with a cone-shaped bottom containing an MASD 10 that is effective in a high rate activated sludge process. As such, this embodiment is a high performance compact reactor that is well suited to treating high strength industrial wastewater by promoting sufficient mixing and aeration to permit a high ram-over rate of tank contents. It is also useful in treating low strength municipal wastewater. High BOD, COD and suspended solid removal efficiency is achieved in this unit by the close and continuous contact of nutrients, dissolved oxygen and biomass.

In addition, as the compressed air rises from tube 20 within the interior of bell 22, wastewater is drawn from the annular space 54. As the water and diffused air rise, the rise rate increases due to the decreasing volume in the upper portion of the truncated cone. As the air and water mixture reach the top of funnel 16, turbulence and pressure increase which results in greater transfer of oxygen into the water and increases the contact time of the total tank contents. As in the FIG. 1 embodiment, the top of cylinder 12 is elevated above the water line 50 of tank 40 and, as a consequence, water and suspended solids flow down between cylinder 12 and the funnel 16.

In high performance compact reactor operation, wastewater enters vertical tank 40 at the top and through cylinder 12. The influent mixes with the upflowing aerated material and is caught in the downwardly flowing current in the annular space 54 between the exterior surfaces 52 of funnel 16 and the interior surfaces 48 of cylinder 12.

When the mixture of water and solids reaches annular space 54 located between the outside of the bottom rim of bell 22 of funnel 16 and the bottom of cylinder 12, some suspended solids and water are pulled back into the interior of funnel 16. Effluent water, substantially free of suspended solids, is displaced by the influent and flows upwardly between the outer surface 56 of cylinder 12 and interior surface 58 of tank 40. When the effluent water reaches the top rim of annular clarifier 62 located near the top of vertical tank 40, it flows into an annular trough of clarifier 62 and out final effluent weir 44. Again, the MASD design allows water and solids to separate at annular space 54 below the water surface, rather than from the upper surface of the water. Separation and clarification thus occur at the annular space 54.

An aeration zone exists in the interior of funnel 16 and extends into cylinder 12 above the hollow neck 24. A clarification zone 60 exists between the outer surface 64 of cylinder 12 and the inner surface 66 of tank 40. A separation zone exists at the annular space 54 which is at the junction of the base of cylinder 12 and the exterior and base of bell 22 and extends to the clarification zone.

As the water, now substantially free of the settled solids, rises upwardly in the containment zone 60, it eventually reaches clarifier 62 and then effluent weir 44. Assisted by the flowing current created by the upward flow through funnel 16, some of the separated solids are pulled back into bell. There is no return activated sludge in this treatment process because the mixed liquor suspended solids do not leave the tank; instead they remain in constant contact with the tank nutrients.

Advantages of a high performance component reactor in accordance with this invention, compared to conventional activated sludge treatment, include high BOD, COD and suspended solid removal rates, treatment and clarification in single tank with no need for return activated sludge, less space than is otherwise required for treatment absent the MASD, a lower capital investment and lower operating cost per liter of effluent as a result, and/or anoxic treatment in a single tank.

Anoxic treatment can proceed within the bottom zone of the tank at the same time aerobic treatment is taking place within the aeration zone. Effective anoxic treatment is accomplished by moving water from tank cone 42 and returning it to the aeration zone at the top of the tank 40.

Also shown in FIG. 2 is an influent line 68 through which influent to be processed by introduction into the tank cone 42 is supplied. There is an air supply line 70 to supply air for aeration in tube 20, a valve 72 for allowing removal of excess waste activated sludge to drain 46, a valve 74 for re-circulating anoxic water, and an anoxic water return pump 76.

USING AN MASD IN GRIT SEPARATION AND REMOVAL

By installing an MASD in a tank proportionally smaller in size, removal of inorganic solids, i.e., grit, can be efficiently accomplished before a sludge is sent to an activated waste treatment facility within a short retention time (between about 10 and 20 minutes). The MASD is sized to achieve such a timing, but is otherwise the same as is used for the activated sludge process.

Grit is removed at the bottom of the tank. By attaching a solenoid valve (not shown) to an electronic timer, grit can be removed by opening the valve for short periods, a few seconds at a time, and as often as required. It is best to place a bar screen or other screening device ahead of the grit tank to remove large floating and settling materials. It is also useful to employ coarse bubble aeration at the bottom of tank 40 to separate the grit from organic material and water of the sludge.

USING AN MASD IN ANAEROBIC TREATMENT OF PRIMARY SLUDGE AND SECONDARY ACTIVATED SLUDGE

Figure 3:
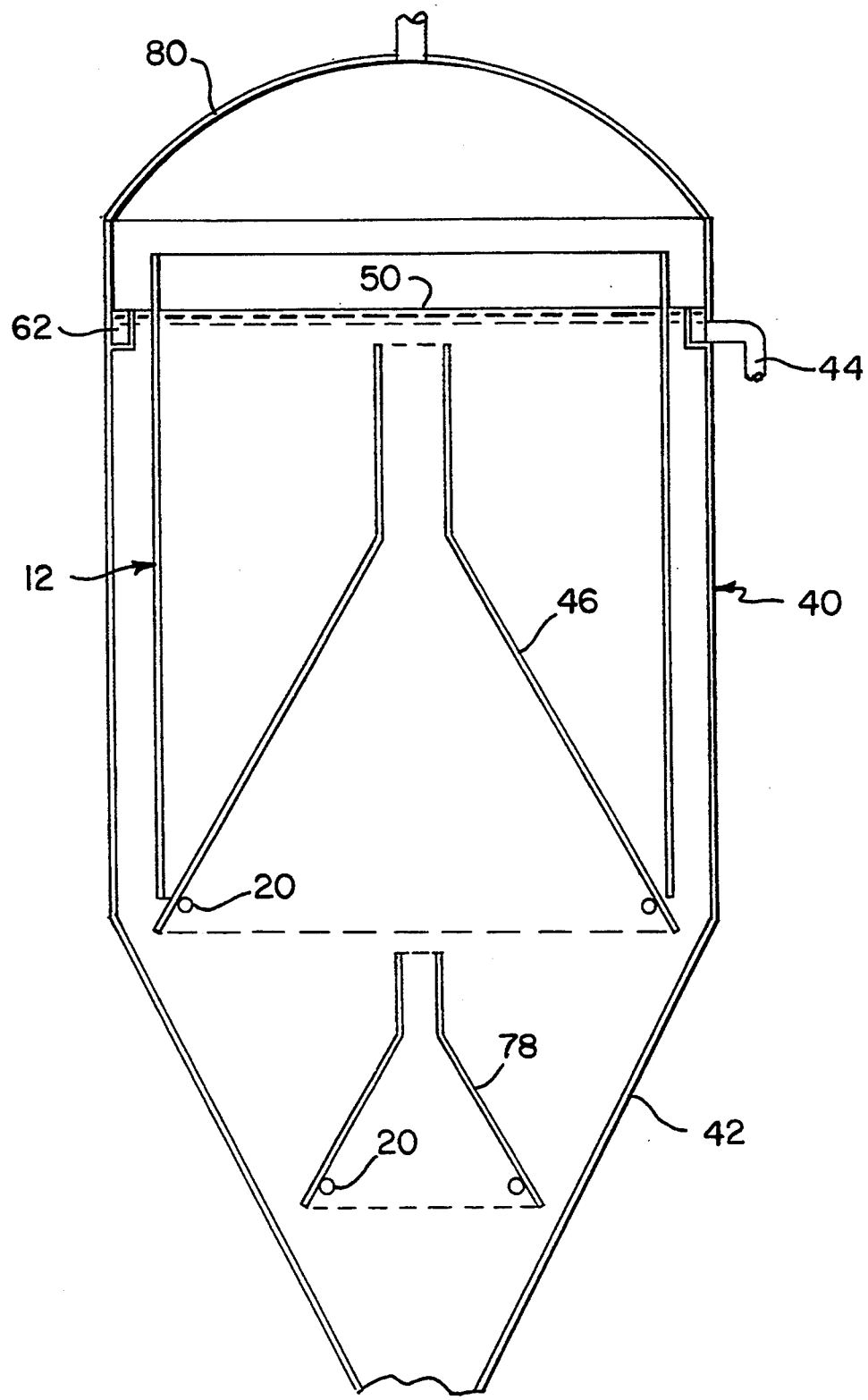
FIG. 3 is a vertical cross section of a larger MASD and a smaller MASD aligned in a closed vertical pre-treatment tank in accordance with another embodiment of the present invention. The MASD and tank are symmetrical about their vertical axes. For the sake of brevity, the influent and effluent discharge elements are not shown.

FIG. 3 shows the same MASD components as FIG. 2, but is modified as follows: By substituting methane gas for air in tube 20 to achieve the mixing and separating of solids from liquid and by placing a dome cover 80 on top of tank 40, the FIG. 3 embodiment of the invention can be operated to attain a high rate of anaerobic digestion. High rate anaerobic digestion requires constant mixing, so that nutrients within the water are in constant contact with the microorganisms for conversion to gas.

A smaller MASD 78 serves as a digester to make possible not only complete mixing of the tank contents, but high rate turn-over as well, i.e., making it possible to turn over the entire tank contents many times per hour. The effluent is clarified as discussed above, but will still contain dissolved solids and BOD and may require further treatment. Sludge remains until discharged by opening a valve (not shown) located at the bottom of tank cone 42 of tank 40. MASD 78 is below the MASD 10 within tank cone 42. A gas diffuser tube 20 is also arranged in and about the base of smaller MASD 78.

When MASD 78 is used in such an anaerobic treatment process, the advantages include complete tank mixing, high volume turn-over rate, efficient conversion of nutrients to methane gas, and high processing rate so that the size of the overall digestion unit can be smaller than otherwise would be necessary. Effluent sludge may be expected to contain lower volatile solids (below 50%) and higher inorganic solids as compared to conventional mixed or unmixed anaerobic digesters.

USING AN MASD IN PRE-TREATMENT

Liquefying sludge can be a process of subjecting primary sludge and secondary activated sludge or waste anaerobic sludge to low levels of dissolved oxygen (0.30 to 0.50 ppm), where bacteria (facultative anaerobes) become the dominant organisms and, as a result of their activity, produce enzymes capable of dissolving the protein bodies of the secondary activated or waste sludge and organic solids contained in the primary sludge. Facultative anaerobes can utilize dissolved oxygen from the water (as do aerobic bacteria), but can also utilize oxygen from their food source, such as nitrates or sulfates, etc. Strict anaerobes can only receive their oxygen from their food supply.

A pre-treatment vertical tank is employed to provide anoxic treatment, which requires maintaining a low level of dissolved oxygen in the wastewater, so that bacteria can consume a large portion of the solids from the wastewater prior to entering an activated sludge treatment or anaerobic process. As a consequence, greater efficiency in BOD removal can be expected. Anoxic treatment benefits some organisms (facultative anaerobes) at the expense of others (strict anaerobes and aerobic bacteria).

An equalization tank (surge tank) is often employed to reduce peak flows in the treatment plant. Water from the equalization tank is pumped to the treatment plant over an extended time, thereby relieving the peak flows. An acidification (fermentation) tank is generally used for converting carbohydrates and organic compounds to simple organic acids (primarily acetic, propionic and butyric). The pre-treatment vertical tank can serve as an acidification (fermentation) tank when placed upstream of an anaerobic methane process by maintaining the dissolved oxygen in the anoxic range (0.30 to 0.50 ppm) so that facultative anaerobes will consume high levels of BOD from the wastewater. The water emerging from the pre-treatment tank can be higher in dissolved nutrients (BOD) and lower in solids (bacteria) than before entering the tank.

Figure 4:
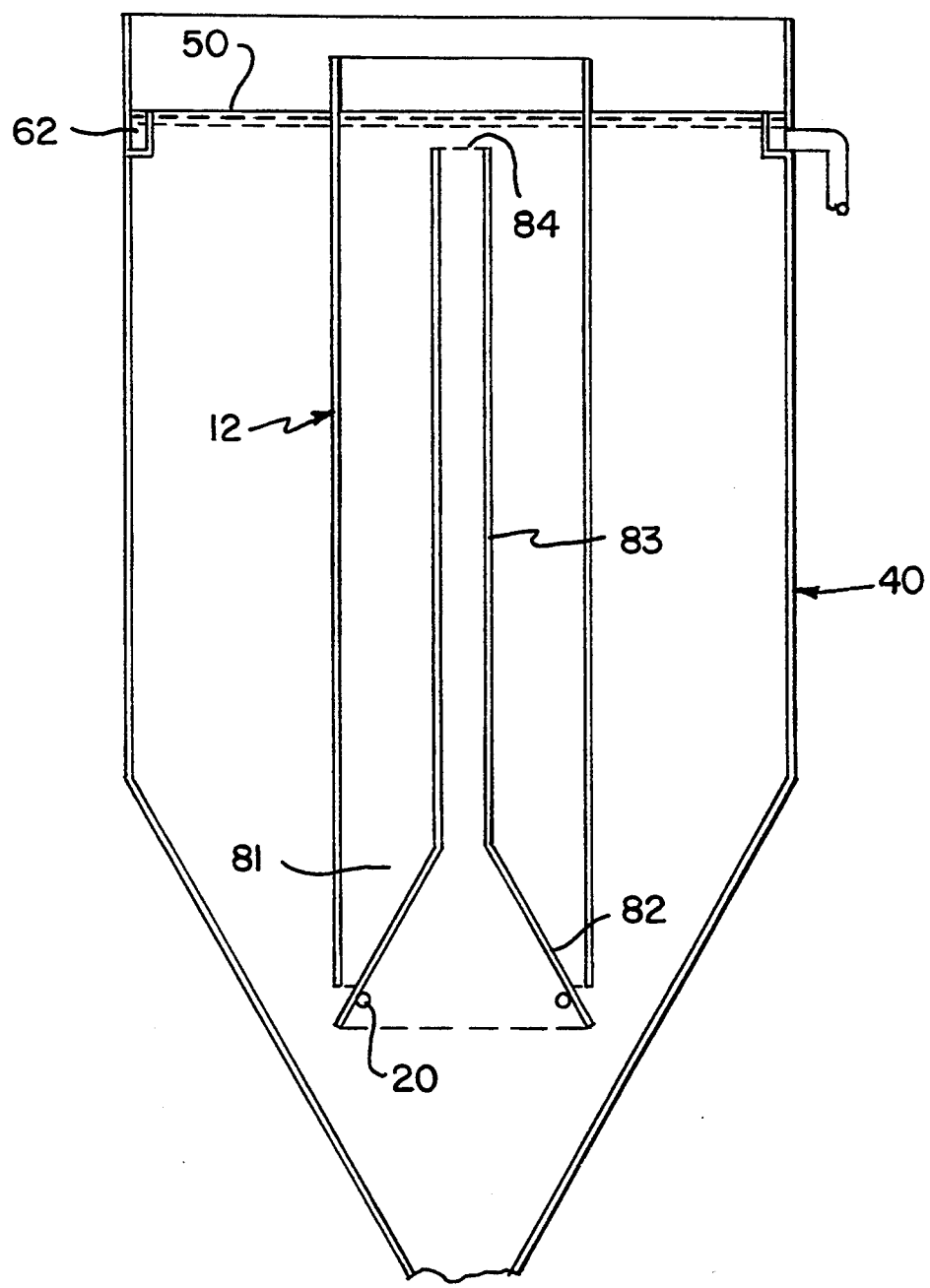
FIG. 4 is a vertical cross section of an MASD in a pre-treatment tank in accordance with yet another embodiment of the present invention. The MASD and tank are symmetrical about their vertical axes. For the sake of brevity, the influent and effluent discharge elements are not shown.

FIG. 4 shows a small MASD 82 installed in a vertical pretreatment tank 40 (equalization or acidification) whose contents can be slowly mixed and supplied with sufficient oxygen to prevent strict anaerobes from dominating the process. The inverted funnel configuration 81 includes a bell portion 82 and a hollow neck portion 83. The bell portion 82 is in the lower portion of the tank 40 and converges toward the neck portion 83. The neck portion extends from the bell portion 82 to the aerated zone 84 within the cylinder 12 in the upper portion of the tank 40 and terminates at an elevation beneath the water line 50. The length of the neck portion 84 is substantially greater than its diameter to channel the constricted upward flow from the bell portion 82 to the aerated zone 84, thereby providing an elongated confined condition within the neck portion 84 suitable for intimate mixing as the constricted flow travels upwardly. By continuous displacement of water from the bottom zone of tank 40 to the top zone of tank 40 into the aerated zone 84 within cylinder 12, rapid reproduction and growth of facultative anaerobes and to a lesser degree aerobic bacteria are promoted, while providing sufficient oxygen to limit or prevent reproduction of strict anaerobes. As the bacteria-laden water flows into the activated sludge process, the nutrients become substantially absorbed by the bacteria that provide much of the ideal food for protozoa and other larger organisms.

USING AN MASD IN HYDROLYZING PRIMARY AND SECONDARY SLUDGE

Liquefying waste activated sludge in anaerobic digestion is the primary limiting factor in an anaerobic process and is the main reason for building large tanks that are designed for retention times of 30 days or more. Primary and secondary sludge can be hydrolyzed by utilizing the same treatment as in the pre-treatment process (see FIG. 3), except that an appropriate nutrient supplement may be added. Such nutrients are conventionally added to control alkalinity, acidity, lack of nitrogen, phosphorous, or other controlling elements to allow biological action to take place. As shown in FIG. 3, the primary sludge and waste activated sludge are pre-treated together in tank cone 42 equipped with a small MASD 78. As a result, ideal conditions can be developed and maintained that will promote hydrolysis of sludge prior to commencement of the anaerobic digestion.

USING AN MASD IN WATER PRECIPITATION

Using the same MASD design as for the activated sludge process of FIG. 1, rapid precipitation of suspended solids in potable water can be achieved with the use of appropriate floc forming chemicals. This is done by mixing water and floc forming chemicals together and then allowing the mixture to enter the turbulence-free zone provided, in which the floc can settle.

MASD USED IN UP-FLOW SLUDGE BLANKET ANAEROBIC DIGESTION

As noted above, up-flow sludge blanket anaerobic digestion is an ideal process for treating high strength industrial liquid waste and, conventionally, the equipment employed utilizes baffles that provide surfaces with sufficient slope to cause biota to form granules as the material rolls down to the bottom of the tank. Further influent fluid enters the vessel through a number of nozzles below the sludge blanket. And as the granulated sludge converts the waste nutrients to gas, a small gas bubble attaches to the surface of a granule. The gas bubble causes the granule to remain floating on the surface of the water until the bubble releases the granule, and conventional techniques separate water, sludge and gas there. Loss of biomass is likely because the separation takes place at the liquid surface.

Figure 5:
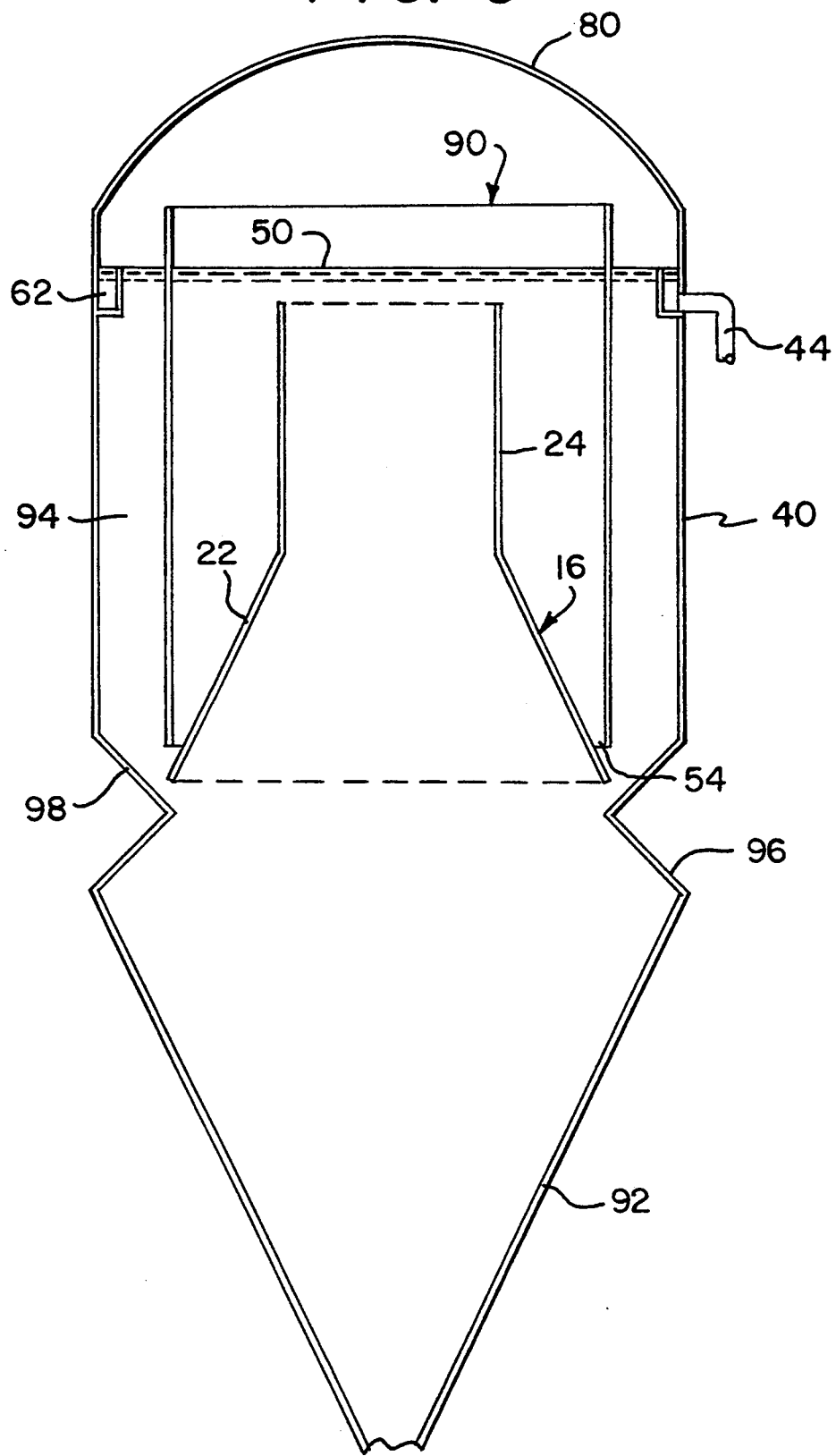
FIG. 5 is a vertical cross section of an MASD positioned in a UASB. For the sake of brevity, the effluent discharge element is not shown, but is at the same location as in the FIG. 1 embodiment.

MASD 90 of FIG. 5 separates water from the sludge granules well below the water surface 50. Unlike conventional UASB designs, sludge granules treated in this MASD cannot flow out of tank 40 from such water surface. When the degassed sludge (biomass) reaches annular space 54, it continues downward until deflecting against an inclined surface 98 of the tank wall, where gravity separates the clarified water from the sludge and the granules settle out. By installing MASD 90 in the upper portion of a UASB design as shown in FIG. 5, rapid conversion of nutrients to methane gas is accomplished with little loss of the biota. By supplementing the influent with nutrients, granules may be formed at a greater rate and the turbidity of the clarified water may be improved. As in the FIG. 1, the top of the cylinder 12 is elevated above water line 50 of the tank and, as a consequence, water and suspended solids either fall back into funnel 16 or flow down between cylinder 12 and funnel 16.

FIG. 5 also shows a digester 92 beneath MASD 90. To prevent gasborne sludge from entering into the containment zone 94, which extends between the outwardly facing surface of cylinder 12 and inwardly facing surface of tank 40, the top of the digester 92 inclines inwardly and upwardly along line 96 and the bottom of tank 40 inclines inwardly and downwardly along the line 98 to meet line 96. This meeting place is spaced away from and beneath the lower end of the outwardly flaring bell 22 of MASD 90. Thus, the housing of the tank 40 and digester 92 comprise a single housing unit.

As fresh influent enters the digester, it is consumed or absorbed by the anaerobic bacteria present in the digester. When biogas is given off, gasborne sludge rises with the biogas, leaving behind a void that is filled by the settled solids returning from the separator. The rate of volumetric flow of the fresh influent and the discharging effluent are about the same. There is continuous circulation of the contents of the UASB, so that the volume of such contents remains about the same at all times.

The presence of suspended solids in the wastewater being treated is detrimental to efficient anaerobic digestion, because these solids plug or coat fixed-film media, on which bacteria grows. Therefore, provision should be made to clean the UASB of suspended solids periodically. Such cleaning may involve introducing a methane gas (e.g., that which is formed by the biogas) in place of the influent to create turbulence within the UASB. Even the introduction of water can serve to create such turbulence. When the contents of the UASB are sufficiently shaken because of the turbulence, the suspended solids dislodge from the fixed film media, leaving the bacteria free to grow again on the media. Such introduction may take place at the bottom of the digester, or centrally therein.

Figure 6:
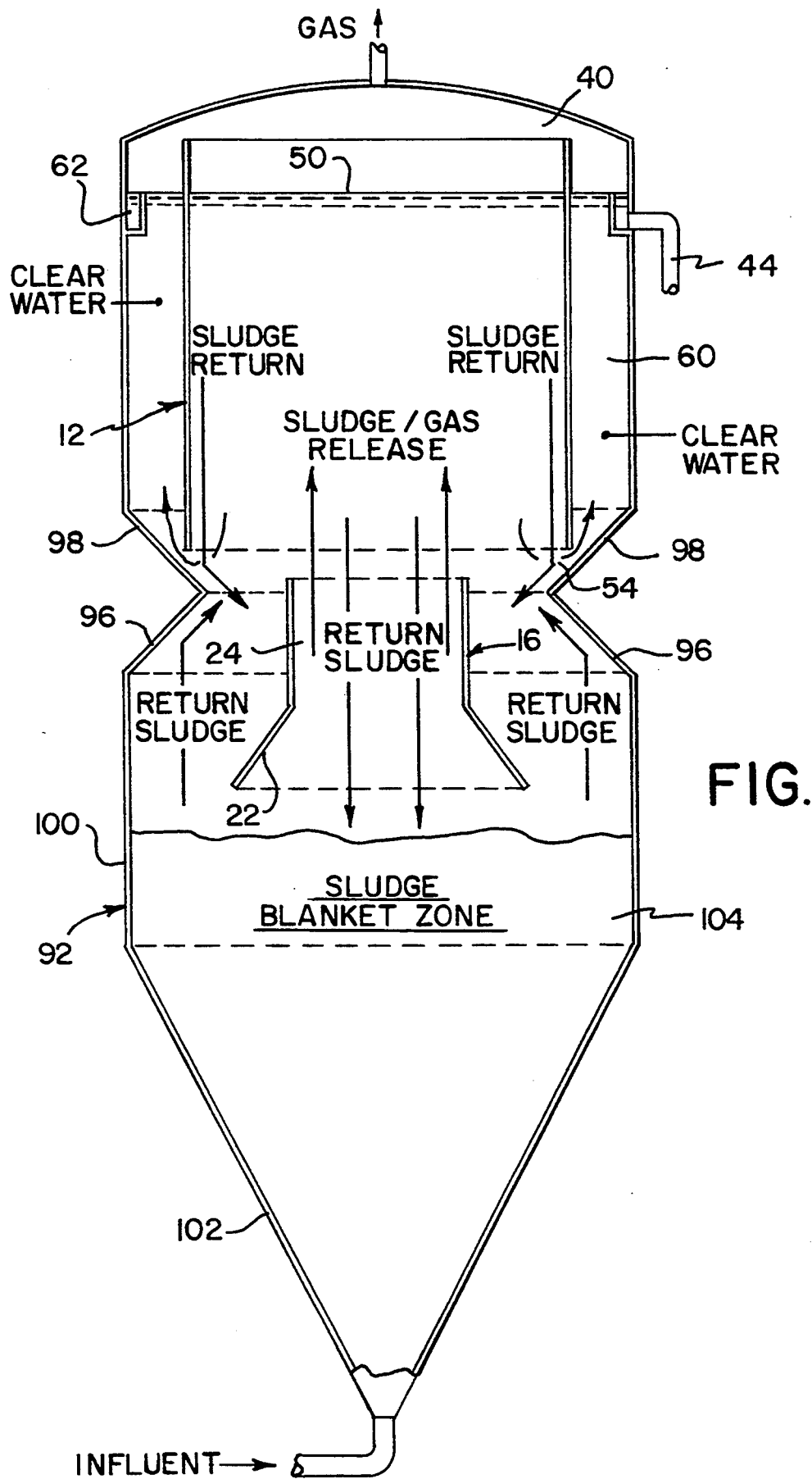
FIG. 6 is a cross section of yet another MASD and is a variation of the FIG. 1 embodiment.

FIG. 6 is a variation of FIG. 5 in that use of funnel 16, with its bell 22 located within the digester 92 and the hollow neck 24 extending into the separator tank housing 40, is shown located at an elevation which is relatively lower than that of FIG. 5. The digester 92 is also shaped differently; there is a substantially cylindrical region 100 between the inclined surfaces 96 and the inwardly sloping conical walls 102 towards the bottom of the digester. Without funnel 16, the upward and downward flows still occur, but the constriction of the flow is not as pronounced as would be the case with the funnel. Nevertheless, some constriction still occurs by virtue of the inclined surfaces 96. A sludge blanket zone 104 extends to a height about midway in the substantially cylindrical region 100.

FIG. 6 also shows a cylinder 12 that defines a containment zone 60, access to which by upward gasborne flow being effectively blocked by inclined surfaces 96. When the downward flow of degassed solids impinges against the tank's incline 98, most solids settle out and the remainder in water is directed through annular space 54, upwardly into the containment zone 60 for subsequent discharge. The fluid level (water line) 50 is at a higher elevation, preferably, than that of the effluent weir 44. A clarifier 62 is also provided at the top of the containment zone 60, interposed between the containment zone and the effluent weir 44. Influent enters from the bottom of the digester 92.

A smaller funnel 78 may also be added to this embodiment at the same relative location as in FIG. 3, preferably having a wider neck for directing the gasborne sludge up the middle of the cylinder 12 and allowing degassed sludge to settle downwardly within a zone outside the upward flow. Such funnel, however, would not need any diffuser tube 20, unlike the FIG. 3 embodiment.

The digester shape in FIG. 6 effectively mimics the shape of funnel 16, for example, FIG. 1 and affords an annular space like annular space 54 in FIG. 1. As a further alternative, therefore, the funnel 16 may be dispensed with as long as this mimicking arises.

Figure 7:
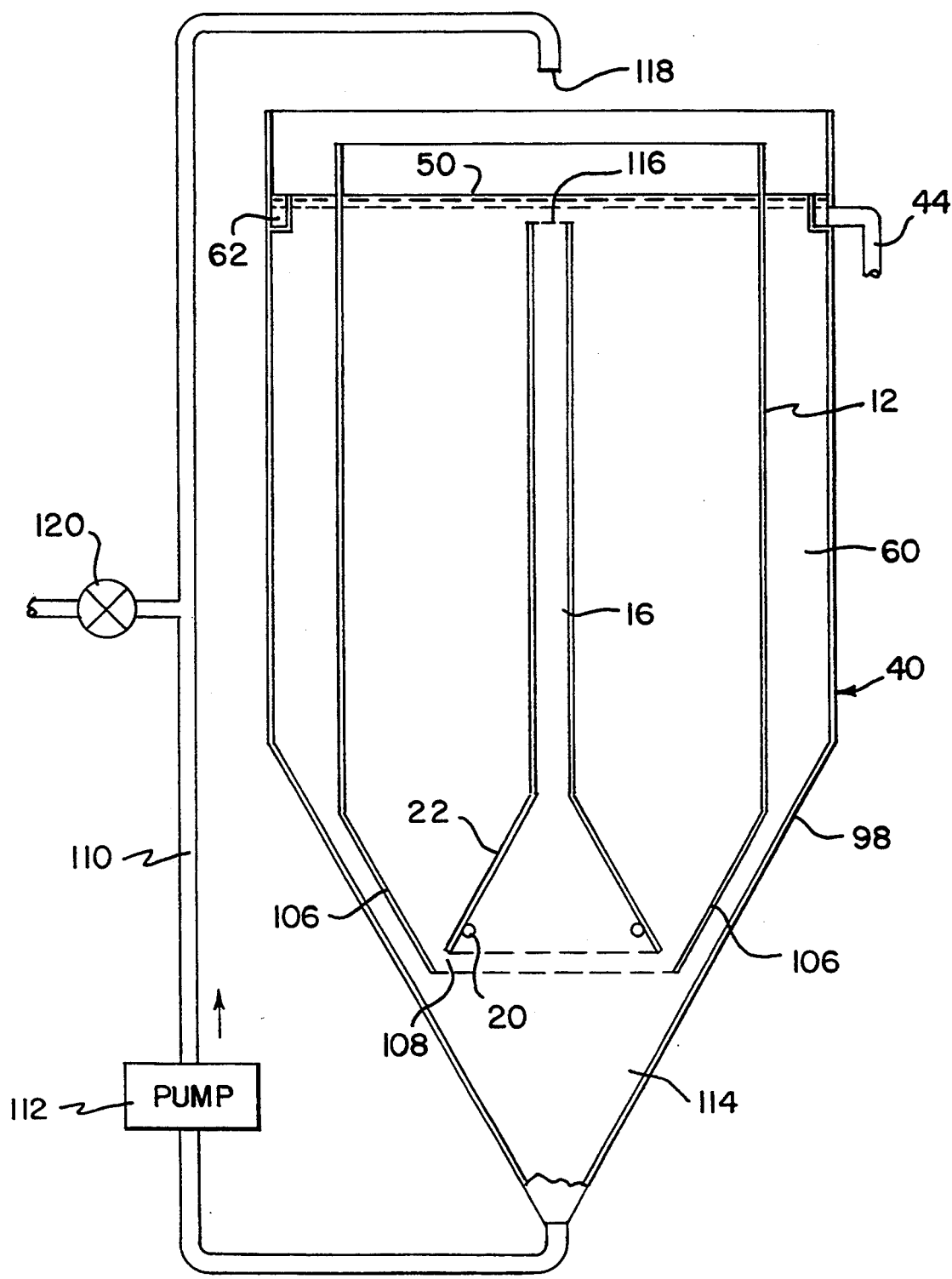
FIG. 7 is a cross section of another MASD.

FIG. 7 is a variation of the FIG. 1 embodiment in that cylinder 12 has a sloping surface 106 that extends into a position between the tank's incline 98 and the path of the downward and outward solids flow from the exterior of the bell. Bell 22 is shown situated at a relatively low elevation within the tank 40 as compared to the FIG. 1 embodiment. The base of bell 22 terminates at an elevation between the elevations of the upper and lower ends of the tank's incline 98. To reach the containment zone 60, the remainder of the mixture left after the settling of most of the solids must flow through the gap 108, which is between the sloping surface 106 and the base of bell 22 and then flow up between the opposite side of the sloping surface 106 and the tank's incline 98. The sloping surface 106 and the tank's incline 98 extend substantially parallel to each other.

Also, in FIG. 7, a sludge recirculation line 110 is shown extending from the conical bottom of tank 40. A recirculation sludge pump 112 forcibly withdraws the contents of the tank, e.g., sludge, from the lower portion 114 of the vessel and elevates it for subsequent introduction back into the upper portion 116 of the vessel through exit 118 of the line 110. A waste sludge valve 120 to open or close the line 110 is shown. In a known manner, interlock controls may be provided to prevent the pump from running if the valve 120 is closed. Alternatively, a recirculation line may be provided in a conventional manner to divert the flow from between the pump and the valve and recirculate it back into the inlet side of the pump to allow the pump to operate continuously.

Electronic controllers and timers are available from many manufacturers for controlling the internal environmental conditions of tank 40 in any of the embodiments so as to sustain the active waste organisms. One example is a ChronTrol XT-4 electronic power switching time controller microprocessor based, supplied by Cole-Parmer Instrument Company, Chicago, Ill. This unit will operate four circuits and provides up to 20 different programs. One circuit is used as a cycle timer for controlling the influent pump and another circuit as a cycle timer for controlling the desired amount of mixing and aeration. A third circuit is used as a cycle timer for removing sludge and the fourth circuit is used as a cycle timer to control the amount of water pumped from the bottom cone to the aeration zone in the containment tube. By addition of electronic sensing devices such as conventional flow meters, pH indicators, dissolved oxygen recording devices, samplers to measure influent parameters, and laboratory analysis, such environmental conditions may be maintained within the tank in a conventional manner to enable the active waste organisms to thrive.

The multiple funnel concept of FIG. 3 may be applied to any of the other embodiments. For larger diameter tanks, it may be desirable to provide additional but smaller funnels below the basic MASD assembly to help drive the upward flow. Each funnel may have its own associated air or gas tube.

In all the embodiments, the flow is in effect guided to follow a particular route. This route includes a path followed by the rising gasborne mixture, a path following by the falling degassed mixture (downward and outward), deflection by surfaces which promotes solid settling, and a path of a rising remainder of the mixture (after solid settling) through a containment zone before reaching the effluent weir or discharge. Preferably, a clarifier is arranged upstream of the effluent weir or discharge at the top of the containment zone travelled by the remainder of the mixture to clarify the mixture of waste organisms and prevent "short-circuiting".

The settled solids aggregate to fall to the bottom of the vessel for subsequent removal, or to become part of the upward flow of fresh gasborne mixture that stems from the introduction of fresh influent. Preferably, the fresh influent displaces substantially the same volume that is discharged through the effluent weir.

A mechanical mixer (e.g., paddle type) may be employed to stir or mix the contents of the tank instead of or in addition to aerating with an aeration element such as the gas diffuser 20. Such a mechanical mixer, for instance, may be used for promoting mixing with respect to the embodiments involving anaerobic treatment.

While the foregoing description and drawings represent the preferred embodiments of the present invention, it will be understood that various changes and modifications may be made without departing from the spirit and scope of the present invention.

What is claimed is:

1. An apparatus for circulating and separating a body of fluid containing a mixture of solid waste, the apparatus comprising:

an elongated vessel with a housing having an internal volume defined by an inwardly facing surface of the vessel, the housing having an influent opening for introducing influent into the internal volume of the vessel and an effluent opening for discharging effluent out of the internal volume of the vessel;

means for creating circulation of the body of fluid within the internal volume of said vessel, said creating circulation means including means for gassifying the body of fluid to produce a gasborne mixture and an upward flow of the gasborne mixture within the internal volume, means for degassing the gasborne mixture to produce a degassed mixture and permit a downward flow of the degassed mixture within the internal volume; and means for guiding circulation of the body of fluid within the internal volume of the vessel along a predetermined route before discharging through the effluent opening, said guiding means including means for channeling said gasborne mixture upwardly from said gassifying means to reach said degassing means, means for deflecting the downward flow of the degassed mixture with a deflection surface to promote settling of solids out of the degassed mixture and leaving a remainder of the degassed mixture substantially free of the settled solids, means for containing said remainder of the degassed mixture within a containment zone, said channeling means having a constriction element configured for constricting the upward flow of the gasborne mixture, said containment zone being interposed between said deflection surface and said vessel surface, and said effluent opening being in communication with said containment zone, said constriction element having an, inverted funnel configuration with a bell portion and a hollow neck portion, said neck portion extending upwardly from said bell portion to terminate at an open top end that is at an elevation spaced from and beneath that of said degassing means, said open end terminating said inverted funnel configuration, said bell portion having an open bottom end that is wider than said open top end of said neck portion, said bell portion having an exterior facing surface that extends from said hollow neck and in a direction such that a projection of said exterior facing surface is toward said deflection surface.

2. An apparatus as in claim 1, further comprising treating means for maintaining a dissolved oxygen level within the water of 0.30 to 0.50 ppm through anoxic treatment, said treating means including said vessel, said constricting means, said creating circulation means, and said guiding means.

3. An apparatus as in claim 1, further comprising treating means for treating municipal wastewater containing the sludge, said treating means including a plurality of serially connected units each having a respective set of said vessel, said creating circulation means, and said guiding means, said units including grit tank means for removing grit, treatment tank means for treating activated sludge, pre-treatment tank means for promoting rapid growth of facultative anaerobes and to a lesser extent aerobic bacteria and for providing sufficient oxygen to prevent reproduction of strict anaerobes and thereby prevent domination by the strict anaerobes, said pre-treatment tank means being arranged upstream of said treatment tank means, said grit tank means being arranged upstream of said pre-treatment tank means.

4. An apparatus as in claim 3, further comprising an additional unit providing means, for hydrolyzing primary and secondary sludge from sources of primary and secondary sludge arranged upstream of said treatment tank means, the primary sludge containing organic solids, the secondary sludge containing active wastewater organisms.

5. An apparatus as in claim 1, wherein said vessel has a lower portion and an upper portion at a higher elevation than said lower portion, said lower portion including an area beneath said bell portion, said upper portion including an area above said bell portion; further comprising means for pumping out contents from said lower portion of the vessel and depositing the pumped out contents into said upper portion of the vessel.

6. An apparatus as in claim 1, wherein said vessel has a lower portion and an upper portion at a higher elevation than said lower portion, said channeling means being arranged within said upper portion of the vessel; and further comprising an additional means for creating circulation within the vessel, said additional means being arranged in said lower portion of the vessel, said additional means including means for additionally gassifying the body of fluid to produce an additional upward flow of a gasborne mixture within the internal volume and means for additionally channeling upward said additional upward flow of the gasborne mixture from said gassifying means, said additionally channeling means including an additional constriction element configured for constricting the additional upward flow of the gasborne mixture.

7. An apparatus as in claim 6, wherein said gassifying means includes means for creating aeration to propel said additional upward flow.

8. An apparatus as in claim 1, wherein said vessel has a lower portion and an upper portion at a higher elevation than said lower portion, said deflection surface extending at an inclined slope from beneath said containment area to a lower elevation beneath said constriction element, said lower portion being bounded by said deflection surface, said bell portion extending within said lower portion of the vessel, said neck portion extending within said upper portion of the vessel.

9. An apparatus as in claim 1, wherein said vessel has a separation portion and a digester portion in communication with each other, said gassifying means including an anaerobic sludge blanket within said digester portion, said bell portion extending within said vessel at an elevation higher than said sludge blanket.

10. An apparatus as in claim 1, wherein said vessel has a separation portion and a digester portion in communication with each other, said gassifying means including an anaerobic sludge blanket within said digester portion, said bell portion extending within said digester portion at an elevation higher than said sludge blanket, said constriction element being arranged so that a projection of said deflection surface is toward said constriction element.

11. An apparatus as in claim 1, wherein said vessel has a lower portion and an upper portion at a higher elevation than said lower portion, said vessel having an inwardly facing surface extending at an inclined slope from beneath said containment area to a lower elevation beneath said constriction element, said lower portion being bounded by said inwardly facing surface, said bell portion extending within said lower portion of the vessel, said neck portion extending within said upper portion of the vessel, said deflection surface being spaced from said inwardly facing surface.

12. An apparatus as in claim 11, wherein said containing means includes a containment wall, said deflection surface sloping downwardly from said containment wall, said deflection surface and said bell portion being arranged for constricting the downward flow therebetween because said deflection surface extends to a location beneath said open bottom end of said bell portion so that the downward flow constricts while the flow passes between said bell portion and said deflection surface.

13. An apparatus as in claim 1, wherein said gassifying means includes means for creating aeration within the confines of said bell portion.

14. An apparatus as in claim 1, wherein said neck portion has a length substantially greater than a diameter of said neck portion.

15. An apparatus as in claim 1, wherein said containing means includes a containment wall, said open bottom end of said bell portion being arranged for constricting flow therebetween because of said bell portion extending to a location beneath said containment wall so that the downward flow constricts while the flow passes between said bell portion and said containment wall.

* * * * *